(12) United States Patent
Mukasa et al.

(10) Patent No.: US 6,733,170 B2
(45) Date of Patent: May 11, 2004

(54) MIXER FOR CAPSULE FOR DENTAL RESTORATION MATERIAL

(75) Inventors: Yoshihisa Mukasa, Tokyo (JP); Yoshimasa Suzuki, Tokyo (JP); Michio Kato, Inashiki-gun (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 10/303,018

(22) Filed: Nov. 25, 2002

(65) Prior Publication Data

US 2003/0103409 A1 Jun. 5, 2003

(30) Foreign Application Priority Data

Dec. 3, 2001 (JP) ........................................ 2001-368471

(51) Int. Cl.$^7$ .......................... B01F 11/00; B01F 13/06
(52) U.S. Cl. ....................................... 366/139; 366/217
(58) Field of Search ........................ 366/139, 209–211, 366/213–214, 217, 219, 602; 433/90, 91

(56) References Cited

U.S. PATENT DOCUMENTS

| | | | |
|---|---|---|---|
| 1,774,257 A | * 8/1930 | English ........................ 366/217 |
| 3,559,961 A | 2/1971 | Bergendal | |
| 3,679,184 A | * 7/1972 | Woodham et al. ........... 366/219 |
| 3,749,390 A | * 7/1973 | Schubert ..................... 366/212 |
| 3,815,115 A | * 6/1974 | Inque ......................... 366/142 |
| 3,985,307 A | * 10/1976 | Ebbert et al. ............... 366/602 |
| 4,199,866 A | * 4/1980 | Drury .......................... 366/139 |
| 4,586,292 A | * 5/1986 | Carroll et al. ............... 366/219 |
| 4,732,739 A | * 3/1988 | Yamamura ................... 366/602 |
| 4,871,261 A | 10/1989 | Randklev | |
| 5,167,448 A | * 12/1992 | Herold et al. ................ 366/213 |
| 5,499,872 A | * 3/1996 | Baxter ......................... 366/213 |
| 2001/0053511 A1 | * 12/2001 | Aoyagi et al. ................. 433/90 |
| 2001/0055238 A1 | * 12/2001 | Suzuki et al. ................ 366/139 |

FOREIGN PATENT DOCUMENTS

| | | |
|---|---|---|
| EP | 1 159 932 | 12/2001 |
| FR | 2 533 820 | 4/1984 |
| FR | 2 636 834 | 3/1990 |
| JP | 3-193127 | * 8/1991 |
| JP | 2001-246236 | * 9/2001 |
| JP | 2002-35563 | * 2/2002 |
| WO | WO 00/45732 | 8/2000 |

* cited by examiner

Primary Examiner—Charles E. Cooley
(74) Attorney, Agent, or Firm—Oblon, Spivak, McClelland, Maier & Neustadt, P.C.

(57) ABSTRACT

A mixer for capsule for dental restoration material to mix a powder component and a liquid component within a mixing compartment of a capsule having an air-permeable filter without passing the powder and liquid components placed in a site connecting the inside of the mixing compartment to the outside into a mixture without air bubbles quietly, quickly and efficiently, includes a capsule holding compartment for holding the capsule such that the air within the mixing compartment can be discharged out from the air-permeable filter, a rotating unit of capsule holding compartment for subjecting the capsule holding compartment itself to a circular motion in the state that the longitudinal direction of the capsule holding compartment is kept in a constant direction, a driving unit for driving the rotating unit of capsule holding compartment, and a vacuum device connected to the capsule holding compartment.

6 Claims, 8 Drawing Sheets

MIXER FOR CAPSULE FOR DENTAL RESTORATION MATERIAL

BACKGROUND OF THE INVENTION

1. Field of the Invention

The present invention relates to a mixer for capsule for dental restoration material to be used for rendering a mixing compartment in vacuo to mix a powder component and a liquid component with each other in a good state where the mixture does not substantially contain air bubbles, in a capsule for dental restoration material accommodating therein two components of definite amounts of previously weighed power component and liquid component in an isolated state from each other, each constituting a dental restoration material used for filling, cementing, lining and other applications in restoration of a tooth in the dental remedy field.

2. Description of the Conventional Art

In general, a dental restoration material is used for restoration of a tooth, such as filling, cementing and lining. As the dental restoration material, a two-component system material comprising a powder component and a liquid component, which are reacted with each other upon mixing, is usually used. Hitherto, this two-component system dental restoration material was provided for use after appropriately weighing the powder component and the liquid component every time and mixing them with each other. However, in recent years, for the purposes of omitting a weighing work of the powder component and the liquid component and a work for accommodating the dental restoration material after mixing in a syringe for administering it to a site to be restored, there have been developed capsules for dental restoration material, in which definite amounts of the powder component and the liquid component are previously weighed and accommodated in an isolated state from each other, the isolated state is released at a desired time, the both components are mechanically mixed with each other by shaking in a mixer, and the resulting mixture is extruded and administered directly to a site to be restored, such as a tooth cavity, through a nozzle.

As such capsules for dental restoration material, various capsules have been proposed. For example, in a capsule as disclosed in Japanese Patent examined Publication No. 38853/1991, the powder component of the two components is accommodated in a mixing compartment of a capsule main body, and the other liquid component is charged in a pillow formed of a sheet film, which is assembled in a side portion of the mixing compartment accommodating the pillow by means of a clip. Further, a two-component system capsule for mixing and discharge as disclosed in Japanese Patent Laid-Open No. 268555/1987 takes a configuration in which the powder component of two components is accommodated in a mixing compartment within a capsule main body, and the other liquid component is accommodated in a pillow formed of a sheet film comprising a resin, a metal foil, or a laminate of a resin and a metal foil. In any of the capsules having such configurations, when the dental restoration material comprising two components of definite amounts of the previously weighed powder component and liquid component is mixed by shaking in a mixer, air present in the mixing compartment mingles into the mixture, whereby it exists as air bubbles. For this reason, the dental restoration material administered in a dental restoration site such as a cavity of a patient contains the air bubbles, so that these conventional capsules involved various problems including a reduction in the strength and a change in the color tone with respect to the dental restoration material.

Thus, in order to overcome the problems of the conventional capsules for dental restoration material as described above and to prevent the occurrence of a phenomenon in which, during mixing the dental restoration material comprising two components of definite amounts of the previously weighed powder component and liquid component accommodated in the conventional capsule for dental restoration material, air present in the mixing compartment mingles into the resulting mixture, whereby it exists as air bubbles, we, the present inventors proposed in Japanese Patent Application No. 163408/2000 a capsule for dental restoration material in which an air-permeable filter capable of ventilating air within the mixing compartment out the mixing compartment without passing the powder component and the liquid component through is provided in at least a part of a peripheral wall of the mixing compartment.

Also, the present inventors developed and proposed a mixer for capsule for dental restoration material suitable as a unit for mixing with respect to the capsule for dental restoration material in which an air-permeable filter capable of ventilating air within the mixing compartment out the mixing compartment without passing the powder component and the liquid component through is provided in at least a part of a peripheral wall of the mixing compartment, as disclosed in Japanese Patent Application No. 163593/2000.

This mixer for capsule for dental restoration material is a mixer for capsule for dental restoration material to be used for mixing the powder component and the liquid component of the dental restoration material by shaking within the mixing compartment of the capsule for dental restoration material in which an air-permeable filter capable of ventilating out air is provided as an external wall constituting at least a part of the peripheral wall, and has a configuration in which a capsule holding compartment for holding the capsule for dental restoration material in a portion other than the position corresponding to the air-permeable filter is provided, the capsule holding compartment being connected to a vacuum device. According to such configuration, when the powder component and the liquid component are mixed with each other by shaking, while rendering the mixing compartment in vacuo, the mixture becomes a dental restoration material in a good state where no air bubbles exist and can be administered directly to a site to be restored, such as a tooth cavity of a patient.

However, since this mixer for capsule for dental restoration material has a configuration in which the powder component and the liquid component are mixed with each other by shaking through a reciprocating motion while rendering the mixing compartment of the capsule for dental restoration material held in the capsule holding compartment in vacuo, a very large noise is generated during shaking the capsule holding compartment. Further, since it has a configuration in which the powder component and the liquid component within the mixing compartment of the capsule for dental restoration material are mixed with each other by reciprocating the capsule holding compartment, it takes a considerable time to mix the powder component and the liquid component within the mixing compartment in a good state. If the reciprocating speed of the capsule holding compartment is increased in order to shorten this time, the noise becomes larger.

SUMMARY OF THE INVENTION

The present invention is aimed to overcome the above-described defects of the conventional art and to provide a mixer for capsule for dental restoration material which generates a smaller noise during mixing a powder component and a liquid component within a mixing compartment of a capsule for dental restoration material and from which a dental restoration material in a good state where no air bubbles exist in the resulting mixture can be obtained within a short period of time and with a good efficiency.

In order to achieve the above-described aim, the present inventors made extensive and intensive investigations. As a result, it has been found that when a capsule holding compartment for holding a capsule for dental restoration material such that air can be discharged out from an air-permeable filter is kept in a constant direction with respect to the longitudinal direction thereof, and the capsule holding compartment itself is subjected to a circular motion in this state, during mixing a powder component and a liquid component within a mixing compartment of the capsule for dental restoration material, not only a noise generated during mixing is small, but also a dental restoration material in a good state where no air bubbles exist in the resulting mixture can be obtained within a short period of time and with a good efficiency, leading to accomplishment of the invention.

Specifically, the present invention is concerned with a mixer for capsule for dental restoration material to be used for mixing a powder component and a liquid component of a dental restoration material within a mixing compartment of a capsule for dental restoration material having an air-permeable filter, which does not pass the powder component and the liquid component through but can ventilate out air within the mixing compartment, placed in a site connecting the inside of the mixing compartment to the outside, the mixer comprising a capsule holding compartment for holding the capsule for dental restoration material such that the air within the mixing compartment can be discharged out from the air-permeable filter, a rotating unit of capsule holding compartment for subjecting the capsule holding compartment itself to a circular motion in the state that a longitudinal direction of the capsule holding compartment is kept in a constant direction, a driving unit for driving the rotating unit of capsule holding compartment, and a vacuum device connected to the capsule holding compartment.

Further, it has been found to be preferable that, when the rotating unit of capsule holding compartment is constituted of a rotating table that is pivoted rotatably to a fixed axis and is rotated by the driving unit, an axis for capsule holding compartment that is pivoted rotatably to the rotating table in a position far from the fixed axis by a predetermined distance and has the capsule holding compartment fixed thereto, and a rotation power transmitting unit for connecting the fixed axis to the axis for capsule holding compartment such that when the axis for capsule holding compartment goes a round centering the fixed axis, the axis for capsule holding compartment makes one revolution, the capsule holding compartment itself can be subjected to a smooth circular motion in the state that the longitudinal direction of the capsule holding compartment is kept in a constant direction.

Moreover, it has been found to be preferable that, when the driving unit is controlled by a driving control unit for making its rotation number and/or rotation time variable, or when the vacuum device is provided with a vacuum control unit for controlling a decompression degree and/or a decompression time, since the rotation number and/or the rotation time, or the decompression degree and/or the decompression time of the capsule holding compartment can be controlled to be in a suitable condition depending on the dental restoration material comprising various kinds of the powder component and the liquid component to be mixed, or on the quantity of the dental restoration material to be mixed, not only a failure by over-mixing or short-mixing during the mixing works can be prevented, but also a dental restoration material in a good state can be easily obtained only through a simple operation by an operator to set up a suitable condition.

In addition, it has been found to be preferable that, when the vacuum device and the capsule holding compartment are connected to each other by a passage respectively provided in the fixed axis, the rotating table and the axis for capsule holding compartment, not only the air within the capsule holding compartment can be stably discharged out, but also the durability of the whole of the apparatus of the present invention increases; and that, when the vacuum device is an ejector connected to a compressed air supply device of dental unit, since the compressed air supply device of dental unit that is placed in a dental clinic can be used as a power source as it stands, the configuration of the apparatus of the present invention can be made inexpensive and simple.

DESCRIPTION OF THE PREFERRED EMBODIMENTS

The mixer for capsule for dental restoration material according to the present invention and the capsule for dental restoration material to be used in the mixer for capsule for dental restoration material will be described below in detail with reference to the drawings.

Figure 1:
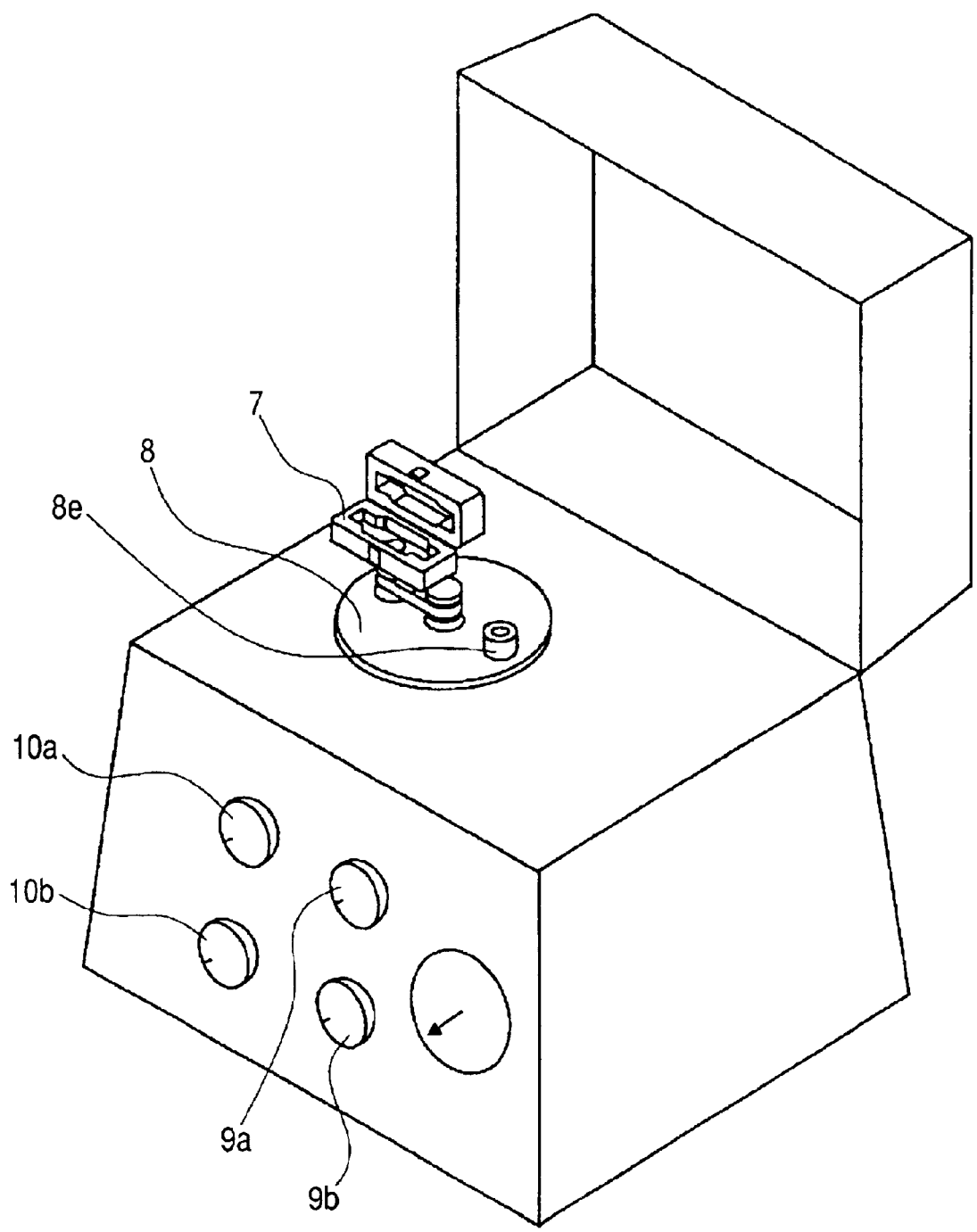
FIG. 1 is a perspective explanatory view of one embodiment of a mixer for capsule for dental restoration material according to the present invention.
Figure 2:
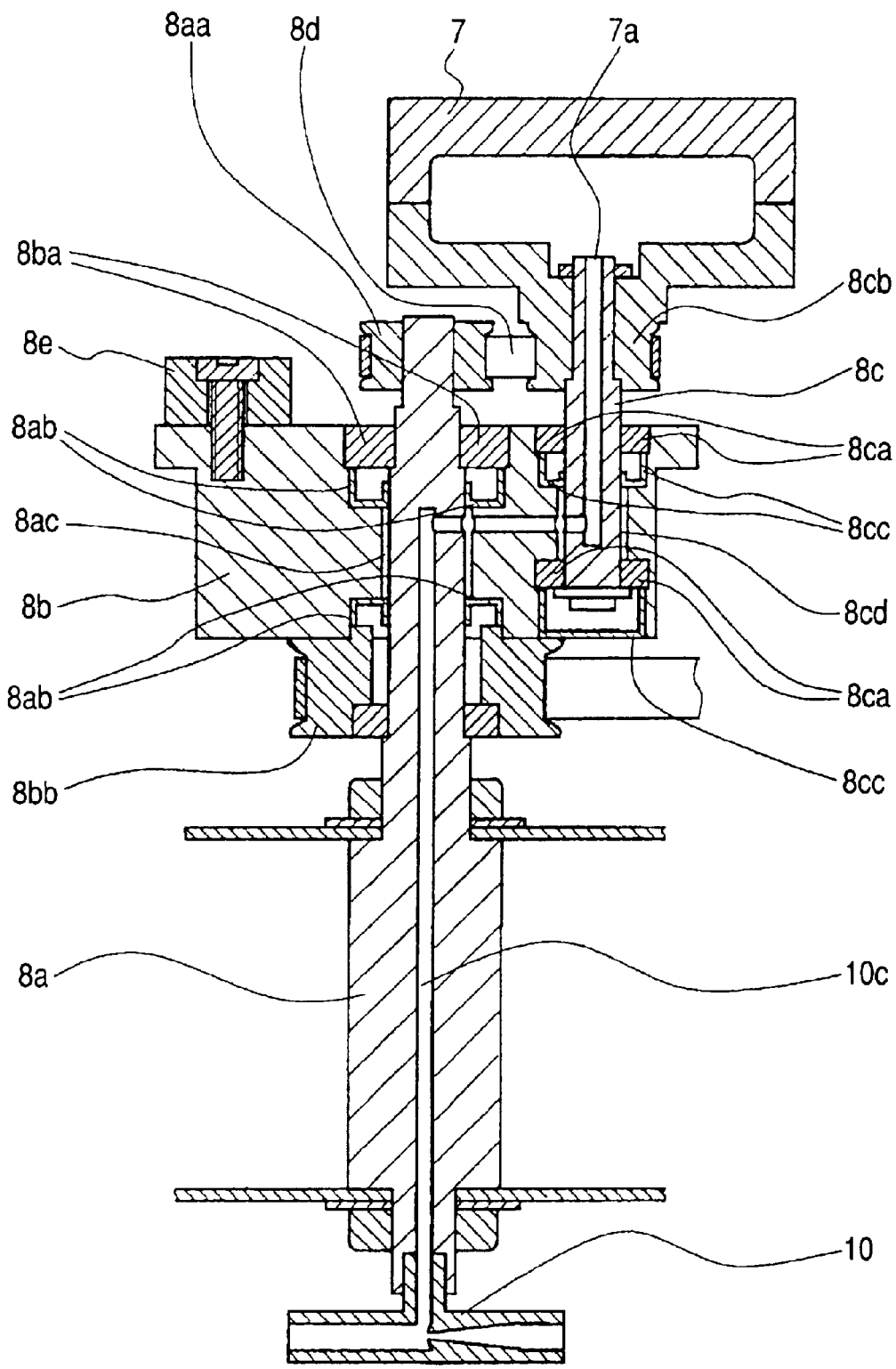
FIG. 2 is a cross-sectional explanatory view to show the relation among a capsule holding compartment, a rotating unit of capsule holding compartment, a driving unit, and a vacuum device in the mixer for capsule for dental restoration material of FIG. 1.
Figure 3:
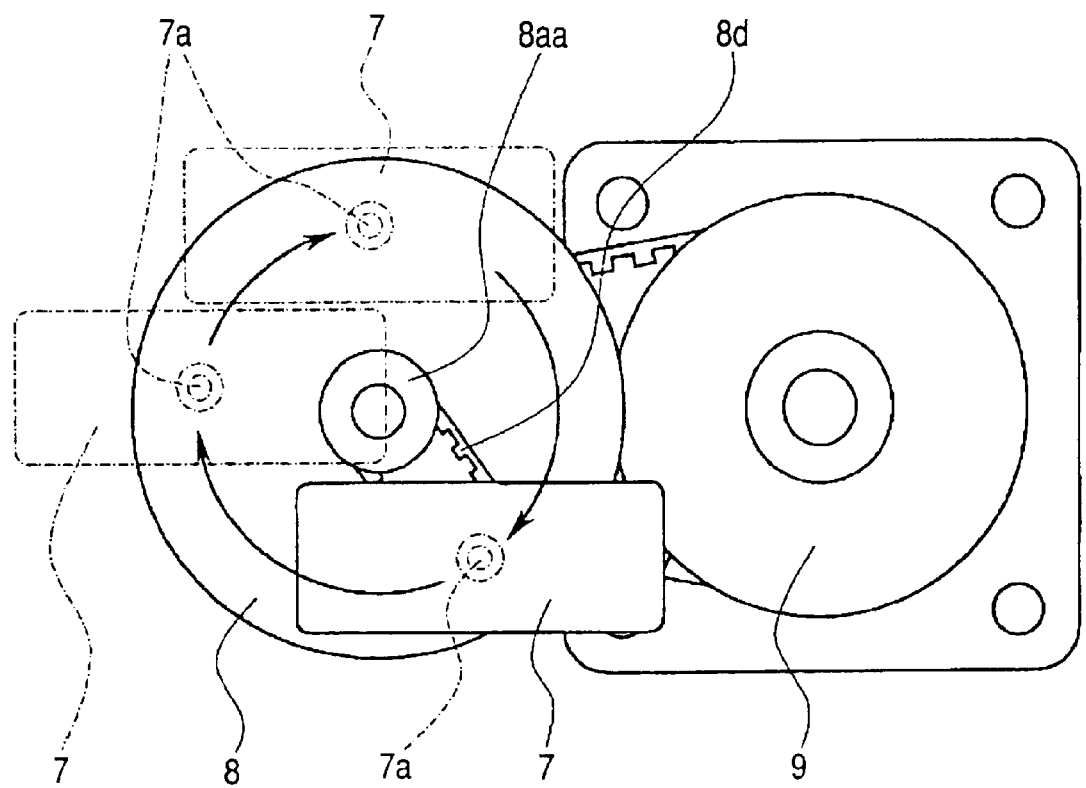
FIG. 3 is an explanatory view to show the movement state of the capsule holding compartment by the rotating unit of capsule holding compartment in the mixer for capsule for dental restoration material of FIG. 1.
Figure 4:
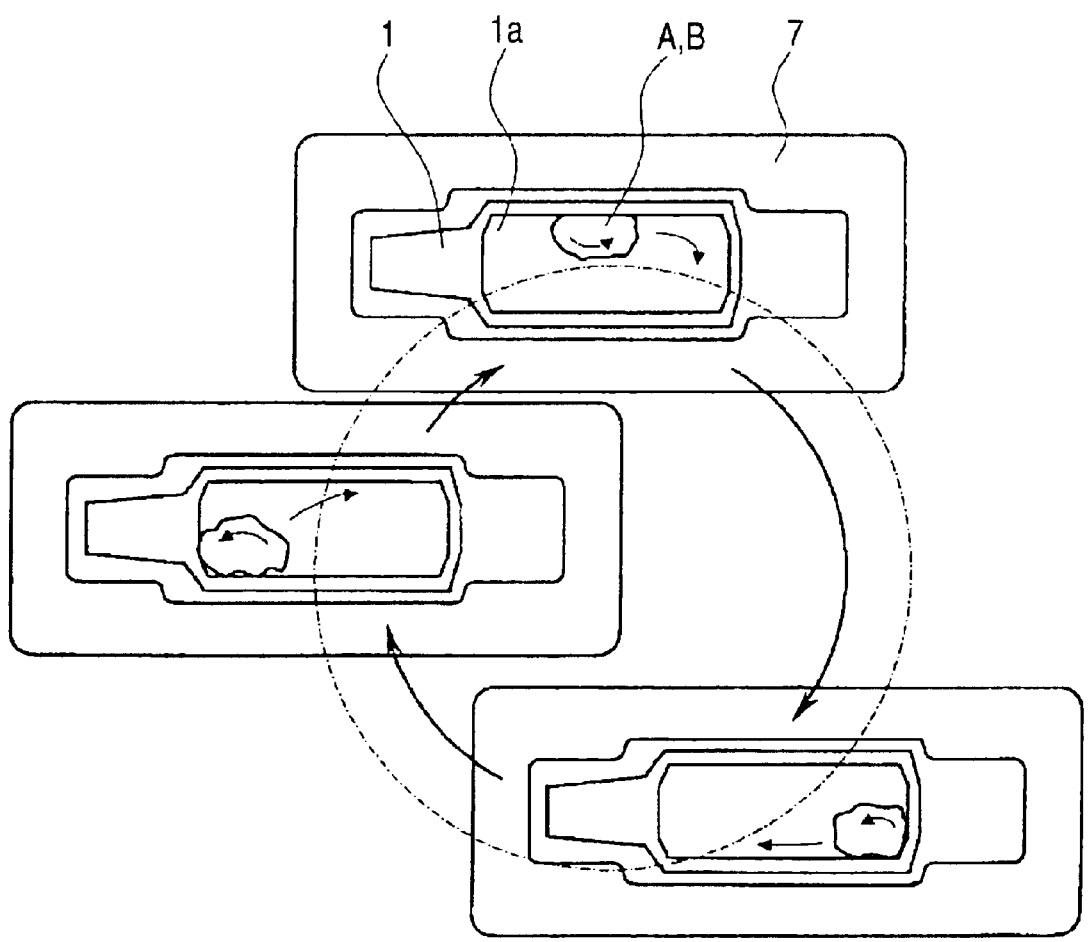
FIG. 4 is an explanatory view to show the state that a dental restoration material is mixed within a mixing compartment of a capsule for dental restoration material held in the capsule holding compartment in the mixer for capsule for dental restoration material according to the present invention.
Figure 5:
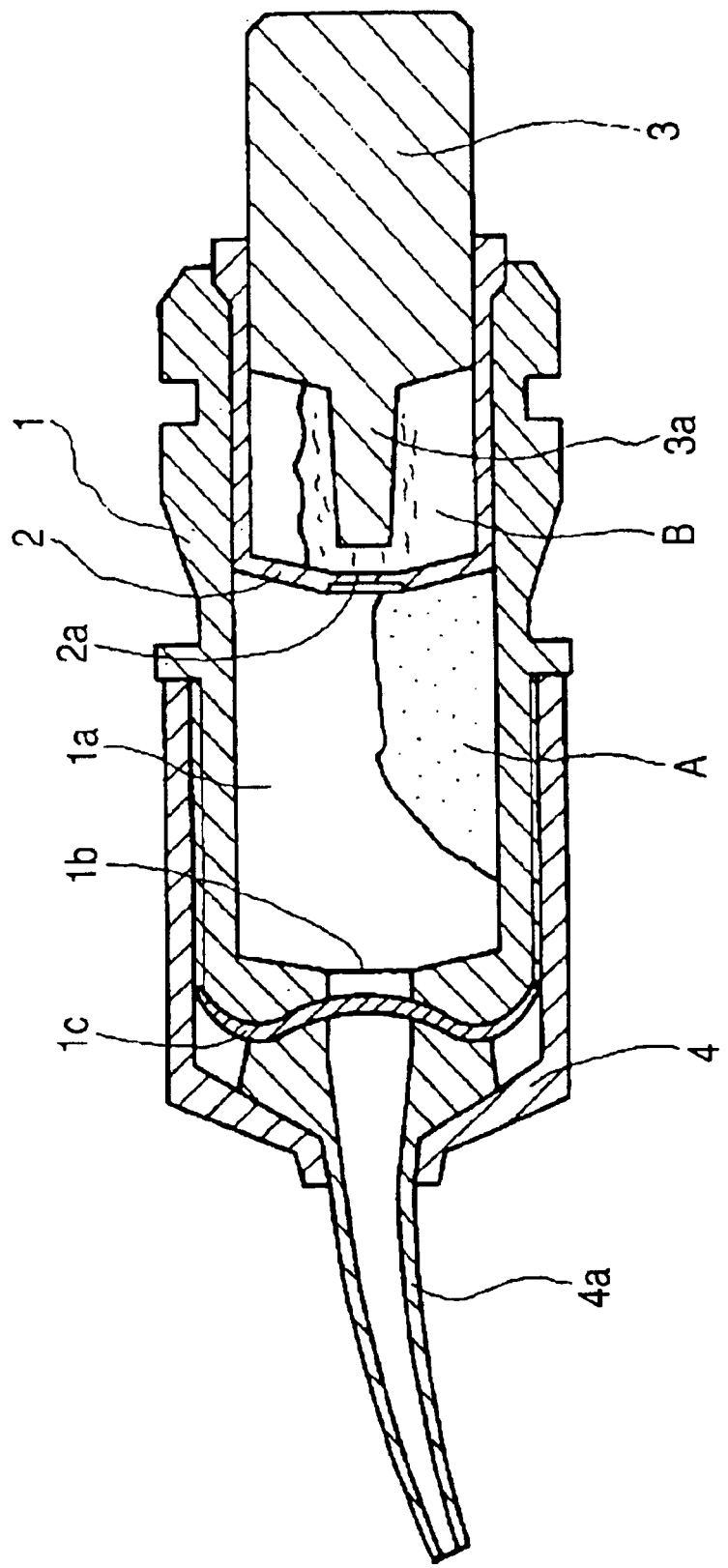
FIG. 5 is an explanatory side cross-sectional view of one example of the capsule for dental restoration material used in the mixer for capsule for dental restoration material according to the present invention.
Figure 6:
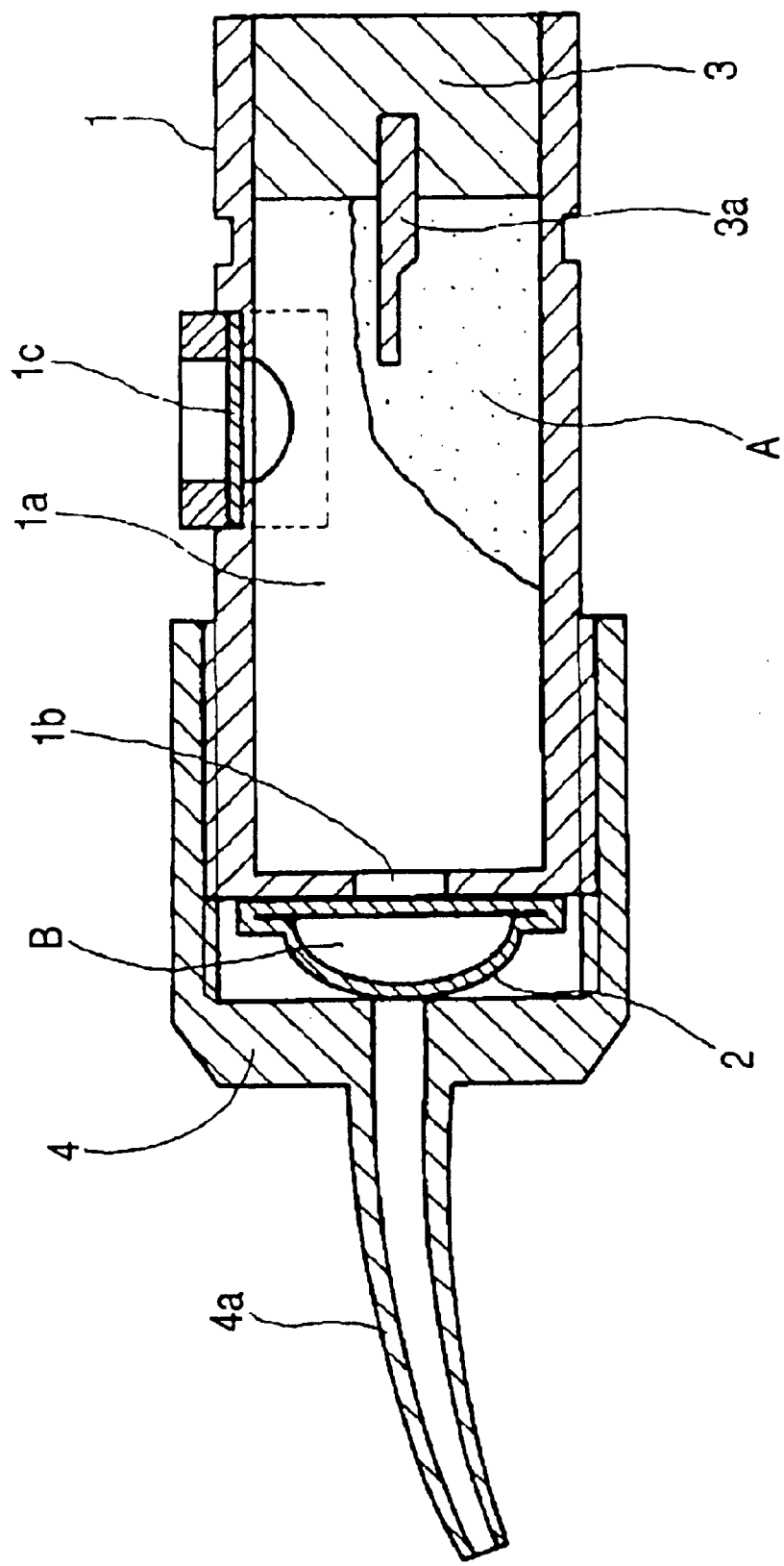
FIG. 6 is an explanatory side cross-sectional view of another example of the capsule for dental restoration material used in the mixer for capsule for dental restoration material according to the present invention.
Figure 7:
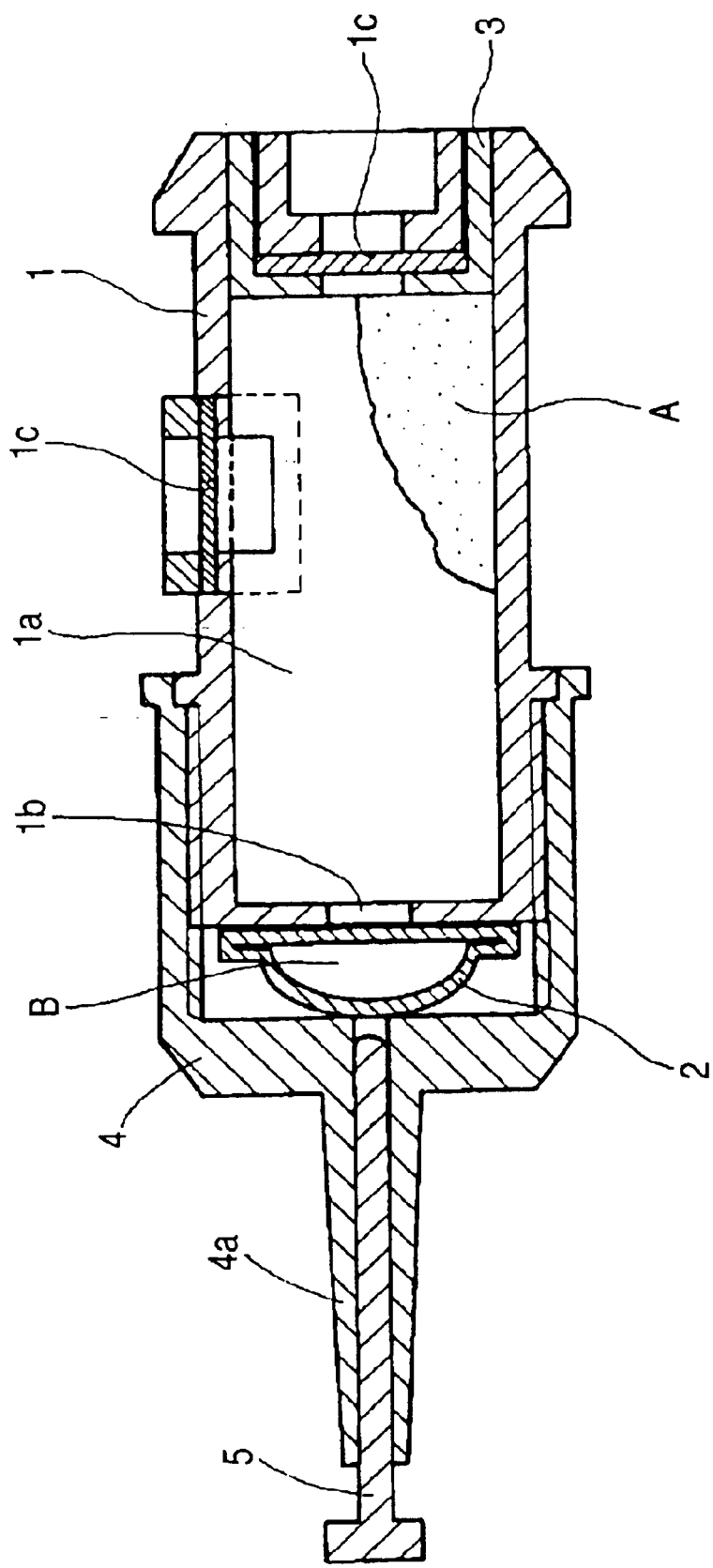
FIG. 7 is an explanatory side cross-sectional view of a still another example of the capsule for dental restoration material used in the mixer for capsule for dental restoration material according to the present invention.
Figure 8:
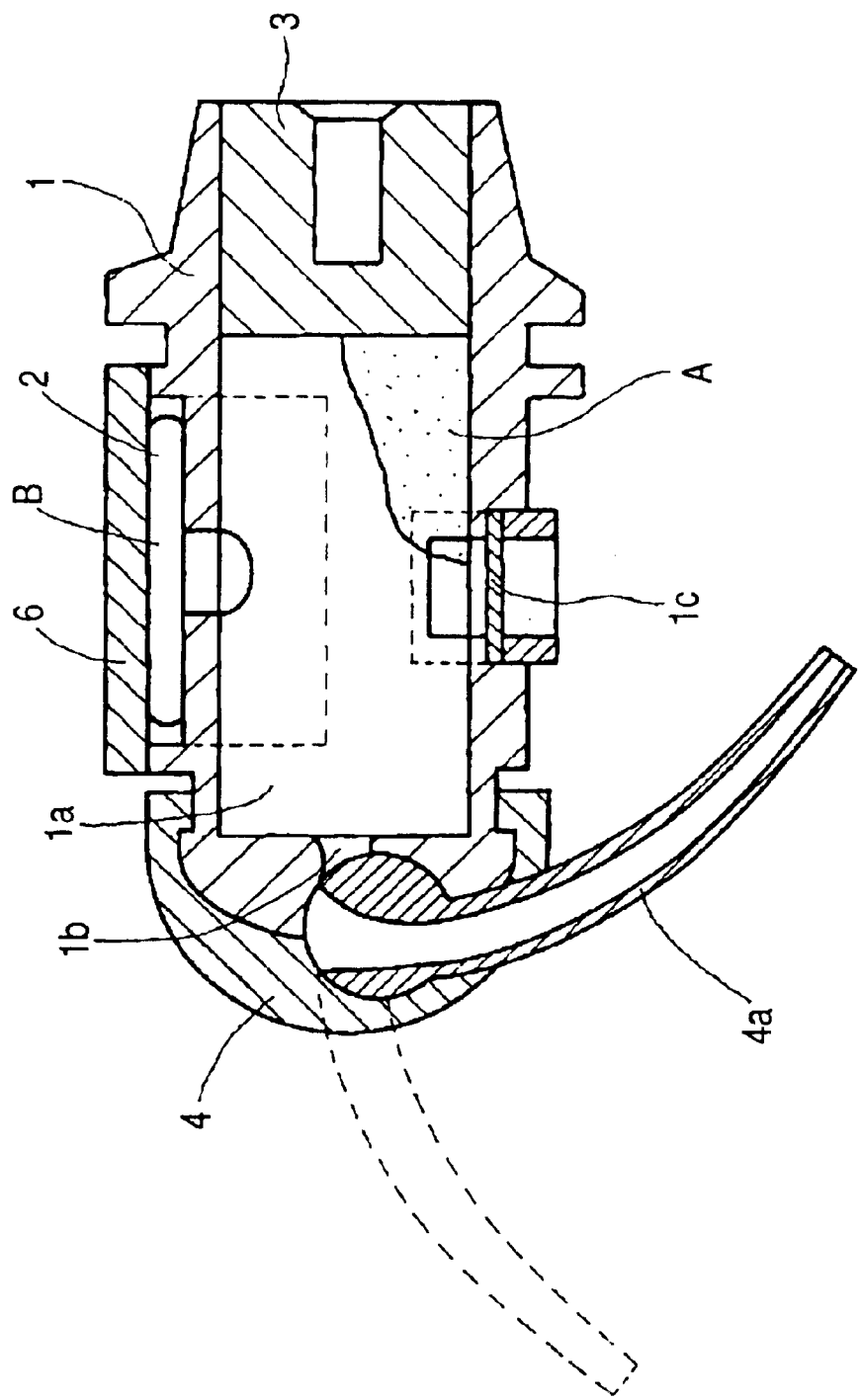
FIG. 8 is an explanatory side cross-sectional view of a still other example of the capsule for dental restoration material used in the mixer for capsule for dental restoration material according to the present invention.

FIG. 1 is a perspective explanatory view of one embodiment of a mixer for capsule for dental restoration material according to the present invention; FIG. 2 is a cross-sectional explanatory view to show the relation among a capsule holding compartment, a rotating unit of capsule holding compartment, a driving unit, and a vacuum device in the mixer for capsule for dental restoration material of FIG. 1; FIG. 3 is an explanatory view to show the movement state of the capsule holding compartment by the rotating unit of capsule holding compartment in the mixer for capsule for dental restoration material of FIG. 1; FIG. 4 is an explanatory view to show the state that a dental restoration material is mixed within a mixing compartment of a capsule for dental restoration material held in the capsule holding compartment in the mixer for capsule for dental restoration material according to the present invention; FIG. 5 is an explanatory side cross-sectional view of one example of the capsule for dental restoration material used in the mixer for capsule for dental restoration material according to the present invention; FIG. 6 is an explanatory side cross-sectional view of another example of the capsule for dental restoration material used in the mixer for capsule for dental restoration material according to the present invention; FIG. 7 is an explanatory side cross-sectional view of a still another example of the capsule for dental restoration material used in the mixer for capsule for dental restoration material according to the present invention; and FIG. 8 is an explanatory side cross-sectional view of a still other example of the capsule for dental restoration material used in the mixer for capsule for dental restoration material according to the present invention.

First of all, the capsule for dental restoration material to be used in the mixer for capsule for dental restoration material according to the present invention will be described.

In the drawings, a numeral 1 is a monolithically formed synthetic resin-made cylindrical capsule main body, in which is provided a cylindrical mixing compartment 1a accommodating therein a definite amount of a previously weighed powder component A to be mixed with a definite amount of a previously weighed liquid component B when the liquid component B flows thereinto. The capsule main body 1 is also provided with an outlet hole 1b for a mixture of the powder component A and the liquid component B as mixed with each other on a center axis in a front end portion thereof. Each of the embodiments as shown in the drawings has a shape such that a cap 4 provided with a nozzle 4a as described later or a cap 4 supporting the nozzle 4a together with the capsule main body 1 can be fixed on an outer surface of the front end portion (a male screw in the embodiments shown in FIGS. 5 to 7 and an engagement concave in the embodiment shown in FIG. 8).

A numeral 2 is a liquid-accommodating tool for accommodating a definite amount of the previously weighed liquid component B. In the embodiment shown in FIG. 5, the liquid-accommodating tool 2 is a monolithically formed synthetic resin-made cylindrical cup that can slide toward the side of the outlet hole 1b for the mixture within the cylindrical mixing compartment 1a of the capsule main body 1 and is provided with a thin film-like seal portion 2a to form a circular flow-in hole for the liquid component B on the center axis in a front end portion thereof. In the embodiments shown in FIGS. 6 and 7, the liquid-accommodating tool 2 is constituted by a bag (pillow) in which the liquid component B is wrapped by a sheet film made by a resin, a metal foil, or a laminate of a resin and a metal foil, to be installed between the capsule main body 1 and the cap 4 provided with the nozzle 4a. In the embodiment shown in FIG. 8, the liquid-accommodating tool 2 is constituted by a bag (pillow) in which the liquid component B is wrapped by a sheet film made by a resin, a metal foil, or a laminate of a resin and a metal foil, to be installed in the outside of an aperture hole provided on the side surface of the capsule main body 1.

A numeral 3 is a synthetic resin-made plunger for extruding the mixture of the powder component A and the liquid component B as mixed with each other within the mixing compartment 1a of the capsule main body 1 toward the side of the outlet hole 1b for the mixture. The embodiment shown in FIG. 5 is an embodiment in which the plunger 3 is a monolithically formed synthetic resin-made one that can slide toward the side of the thin film-like seal portion 2a within the liquid-accommodating tool 2, a rod-like protrusion 3a breaking through the thin film-like seal portion 2a of the liquid-accommodating tool 2 is provided in a front end portion thereof, and after making the liquid component B within the liquid-accommodating tool 2 flow into the mixing compartment 1a of the capsule main body 1, the plunger 3 moves together with the liquid-accommodating tool 2, thereby the rod-like protrusion 3a being inserted into the outlet hole 1b for the mixture of the capsule main body 1. The embodiments shown in FIGS. 7 and 8 are embodiments in which the plunger 3 is a monolithically formed synthetic resin-made one having such a shape that the plunger 3 can slide in the mixing compartment 1a to extrude the mixture within the mixing compartment 1a of the capsule main body 1 toward the side of the outlet hole 1b for the mixture. In the embodiment shown in FIG. 6, the plunger 3 is provided with the rod-like protrusion 3a breaking through the sheet film in the opposite side to the outlet hole 1b of the liquid-accommodating tool 2 in the front end portion thereof.

A numeral 4 is a synthetic resin-made cap having such a shape that it can be fixed to an outer surface of the front end portion of the capsule main body 1 for disposing the nozzle 4a in the front end portion of the capsule main body 1 (a male screw in the embodiments shown in FIGS. 5 to 7 and an engagement protrusion in the embodiment shown in FIG. 8, respectively). The cap 4 includes the embodiments shown in FIGS. 5 and 8 in which when the cap 4 is fixed to the outer surface of the front end portion of the capsule main body 1, it supports the nozzle 4a between the cap 4 and the capsule main body 1 and those shown in FIGS. 6 and 7 in which the nozzle 4a is formed monolithically with the cap 4. Further, while not shown in the drawings, is an embodiments in which the liquid-accommodating tool 2 is to be not necessary to be disposed facing the outlet hole 1b of the capsule main body 1, as in the embodiments shown in FIGS. 5 and 8, and when the nozzle 4a is not to be rotated, the cap 4 is omitted and the nozzle 4a is fixed to the capsule main body 1 by screw engagement or embedding.

In the case where the liquid-accommodating tool 2 is a capsule comprising a bag (pillow) containing the liquid component B wrapped by the sheet film as in the embodiment shown in FIG. 7, a numeral 5 is a through rod previously set within the nozzle 4a provided on the center axis of the cap 4, such that it breaks through the sheet film in the opposite side to the outlet hole 1b of the liquid-accommodating tool 2, thereby enabling to supply the mixture of the powder component A and the liquid component B as mixed within the mixing compartment 1a of the capsule main body 1 into the nozzle 4a.

In the case where the liquid-accommodating tool 2 is a capsule comprising a bag (pillow) containing the liquid component B wrapped by the sheet film as in the embodiment shown in FIG. 8, a numeral 6 is a clip installing the liquid-accommodating tool 2 on an outer portion of the side wall of the mixing compartment 1a of the capsule main body 1. During the use, the clip 6 is pushed toward the direction of the mixing compartment 1a to smash and break the sheet film in the side of the mixing compartment 1a of the liquid-accommodating tool 2 having the liquid component B accommodated therein, thereby enabling to supply the liquid component B into the mixing compartment 1a of the capsule main body 1.

In the capsules for dental restoration material having such various shapes, which can be used in the mixer for capsule for dental restoration material according to the present invention, an air-permeable filter 1c that does not pass the powder component A and the powder component B of the dental restoration material therethrough but can ventilate out air within the mixing compartment 1a is placed in a site connecting the inside of the cylindrical mixing compartment 1a of the capsule main body 1 to the outside.

In the embodiment shown in FIG. 5, the air-permeable filter 1c is placed in the state of clogging a mixture passage connecting the nozzle 4a for directly administering the mixture to a restoration site of a tooth to the mixing compartment 1a; in the embodiments shown in FIGS. 6 and 8, the air-permeable filter 1c is placed on the side wall of the mixing compartment 1a; and in the embodiment shown in FIG. 7, the air-permeable filter 1c is placed on the side wall of the mixing compartment 1a and the plunger 3 extruding the mixture within the mixing compartment 1a toward the nozzle 4a for directly administering it to a restoration site of a tooth. In order to place the air-permeable filter 1c in a site connecting the inside of the cylindrical mixing compartment 1a of the capsule main body 1 to the outside, the air-permeable filter 1c may be held between the capsule main body 1 and the cap 4 so as to close the outlet hole 1b of the capsule main body 1 as in the embodiment shown in FIG. 5. Alternatively, an aperture window may be formed on the side wall of the cylindrical mixing compartment 1a of the capsule main body 1 or the plunger 3 in the side facing the mixing compartment 1a, and the air-permeable filter 1c disposed in this aperture window may be pressed and fixed by a presser that is similarly provided with an aperture window. In this case, it is preferred that the air-permeable filter 1c is provided in a position other than the inner side wall of the mixing compartment 1a constituting a sliding surface with the plunger 3 (the liquid-accommodating tool 2 in the case of the embodiment shown in FIG. 5) that slides and moves within on an inner wall of the mixing compartment 1a.

Usually, the powder component A of the dental restoration material has a particle size of 50 μm or less, and the liquid component B of the dental restoration material has a relatively high viscosity as 220~750 cP as measured under the temperature condition of 23° C. using a B type rotational viscometer. Accordingly, with respect to the air-permeable filter 1c, so far as a material does not pass the powder component A therethrough, it inevitably does not pass the liquid component B therethrough, too. Suitable examples of such materials that can be used include fabric materials textured with fibers such as cellulose fibers, glass fibers, polyfluoroethylene fibers, silicone fibers, and silica fibers; and film-like materials made of nylon, polyester, polyethylene, polypropylene, polycarbonate, polyether sulfone, or a mixture thereof.

Next, the mixer for capsule for dental restoration material according to the present invention, in which the dental restoration material comprising two components of the powder component A and the liquid component B is mixed within the mixing compartment 1a of the capsule for dental restoration material having the configuration as described above, will be described below.

A numeral 7 is a capsule holding compartment for holding the capsule for dental restoration material such that the air can be discharged out from the capsule for dental restoration material having the configuration as described above. The capsule holding compartment 7 has a configuration such that it can close the capsule for dental restoration material in a sealed state by a lid and the like, while holding it, and is connected to a vacuum device 10 as described later. In the case of the embodiment shown in the drawings, the air within the capsule holding compartment 7 closed in a sealed state is discharged out from an air discharge hole 7a provided in a bottom portion thereof.

In order to hold the capsule for dental restoration material such that the air can be discharged out from the capsule for dental restoration material, it may have a configuration such that it can be held in a portion not clogging the front end portion of the nozzle 4a in the case of the capsule for dental restoration material as shown in FIG. 5, a portion not clogging an aperture portion where the air-permeable filter 1c placed on the side wall of the capsule main body 1 is exposed in the case of the capsules for dental restoration material as shown in FIGS. 6 and 8, and a portion not clogging at least one of the air-permeable filter 1c placed on the side wall of the capsule main body 1 and the air-permeable filter 1c disposed in the aperture window of the plunger 3 formed in the side facing the mixing compartment 1a in the case of the capsule for dental restoration material as shown in FIG. 7, respectively.

A numeral 8 is a rotating unit of capsule holding compartment for subjecting the capsule compartment 7 itself to a circular motion in the state that a longitudinal direction of the capsule holding compartment 7 is kept in a constant direction, and is driven by a rotation power of a driving unit 9 as described later.

In the case of an embodiment where the rotating unit 8 of capsule holding compartment is constituted of a rotating table 8b that is pivoted rotatably to a fixed axis 8a and is rotated by a driving unit 9, an axis 8c for capsule holding compartment that is pivoted rotatably to the rotating table 8b in a position far from the fixed axis 8a by a predetermined distance and has the capsule compartment 7 fixed thereto, and a rotation power transmitting unit 8d for connecting the fixed axis 8a to the axis 8c for capsule holding compartment such that when the axis 8c for capsule holding compartment goes a round centering the fixed axis 8a, the axis 8c for capsule holding compartment makes one revolution, a pulley 8aa is fixed to the fixed axis 8a; the rotating table 8b is pivoted rotatably to the fixed axis 8a via a bearing 8ba, and a pulley 8bb is fixed to the rotating table 8b coaxially with the fixed axis 8a; the axis 8c for capsule holding compartment is pivoted rotatably to the rotating table 8b in a position far from the fixed axis 8a by a predetermined distance via a bearing 8ca; the axis 8c for capsule holding compartment or the capsule holding compartment 7 is provided with a pulley 8cb by fixation or monolithic formation; and the capsule holding compartment 7 is fixed to the upper end of the axis 8c for capsule holding compartment, as shown in FIG. 2. Further, the rotation power transmitting unit 8d is constituted of the pulley 8cb provided on the axis 8c for capsule holding compartment or in the capsule holding compartment 7, the pulley 8aa fixed to the fixed axis 8a and having the same diameter as the pulley 8cb, and a timing belt for connecting the both pulleys 8aa and 8cb to each other, such that when the axis 8c for capsule holding compartment goes a round centering the fixed axis 8a, the axis 8c for capsule holding compartment makes one revolution. Moreover, as shown in FIG. 1, when a balance weight 8e is provided on the rotating table 8b in a position of point symmetry with a center of the axis 8c for capsule holding compartment centering a center of axis of the fixed axis 8a, not only the rotational motion of the rotating table 8b becomes stable, but also the life of the bearings 8ba and 8ca can be prolonged, and hence, such is preferable.

A numeral 9 is a driving unit for driving the rotating unit 8 of capsule holding compartment, and instruments for undergoing rotational driving, such as an electric motor and a servo-motor, can be used therefor. In the case of the illustrated embodiment, the pulley fixed to the driving axis of the driving unit 9 and the pulley 8bb of the rotating table 8b of the rotating unit 8 of capsule holding compartment are connected to each other by a timing belt. Further, though in the driving unit 9, the connecting and cutting of an electric source to be supplied may be made merely by a switch and the like, when the driving unit 9 is configured such that it is controlled by a driving control unit for making its rotation number and/or rotation time variable, the rotation number and/or the rotation time under suitable conditions can be obtained depending on the dental restoration material comprising various kinds of the powder component and the liquid component to be mixed, or the quantity of the dental restoration material to be mixed, and hence, such is preferable. The driving control can be carried out by a switch 9a for variable resistance capable of controlling an electric source to be supplied to the driving unit or a switch 9b for timer to be set for a timer.

A numeral 10 is a vacuum device connected to the capsule holding compartment 7, which discharges out the air within the mixing compartment 1a of the capsule for dental restoration material held within the capsule holding compartment 7 through the air-permeable filter 1c by sucking the air within the capsule holding compartment 7 to render the capsule holding compartment 7 in vacuo. The vacuum device 10 may be a usual vacuum pump that is driven by a motor. But, when the vacuum device 10 is an ejector to be connected to a compressed air supply device for a dental unit, a compressed air supply device for a dental unit placed in a dental clinic can be used as a power source thereof, and the system can be of an inexpensive and simple structure. Thus, such is preferable.

When the vacuum device 10 is provided with a vacuum control unit for controlling a decompression degree and/or a decompression time, the decompression degree and/or the decompression time under suitable conditions can be obtained depending on the dental restoration material comprising various kinds of the powder component A and the liquid component B to be mixed, or the quantity of the dental restoration material to be mixed, and hence, such is preferable. In the case where the vacuum device 10 is a usual vacuum pump that is driven by a motor, the vacuum control may be carried out by a switch 10a for variable resistance capable of controlling an electric source to be supplied to the motor or a switch 10b for timer to be set for a timer. Further, in the case where the vacuum device 10 is an ejector, the vacuum control may be carried out by a switch 10a for valve control actuating an electromagnetic valve or a motor valve for controlling a compressed air pressure as a power source to be supplied to the ejector, or by a switch 10b for timer for setting an actuation time of the electromagnetic valve or the motor valve.

The connection between the vacuum device 10 and the capsule holding compartment 7 may be made using a tube, a pipe, etc. But, as shown in FIG. 2, when the vacuum device 10 is connected to the capsule holding compartment 7 via a passage 10c respectively provided in the fixed axis 8a, the rotating table 8b and the axis 8c for capsule holding compartment, not only the air within the capsule holding compartment 7 can be stably discharged out, but also the durability of the whole of the apparatus increases, and hence, such is preferable. In the case where the vacuum device 10 is in the embodiment as shown in FIG. 2, the air within the capsule holding compartment 7 goes from the air discharge hole 7a provided in the capsule holding compartment 7 through the passage 10c provided within the axis 8c for capsule holding compartment, goes through a space 8cd partitioned between gaskets 8cc that are inserted in an upper portion and a lower portion of the bearing of the axis 8c for capsule holding compartment provided within the rotating table 8b, goes through the passage 10c provided so as to connect the space 8cd to a space 8ac partitioned between gaskets 8ab that are inserted in an upper portion and a lower portion of the bearing of the fixed axis 8a provided within the rotating table 8b, and then goes from the space 8ac through the passage 10c provided within the fixed axis 8a to the vacuum device 10.

In order to mix the dental restoration material comprising two components of the powder component A and the liquid component B accommodated within the capsule for dental restoration material having the above-described configuration using the mixer for capsule for dental restoration material having such a configuration according to the present invention, first of all, an operation for making the liquid component B within the liquid-accommodating tool 2 flow into the mixing compartment 1a of the capsule main body 1 is carried out. This operation is carried out in the following manner. That is, in the capsule for dental restoration material of the embodiment shown in FIG. 5, the plunger 3 is slided toward the side of the outlet hole 1b of the capsule main body 1, thereby breaking through the thin film-like seal portion 2a forming the flow-in hole for the liquid component B provided on the center axis of the front end portion of the liquid-accommodating tool 2; in the capsules for dental restoration material of the embodiments shown in FIGS. 6 and 7, the capsule main body 1 is moved toward the side of the cap 4, thereby rupturing and breaking a portion of the side of the outlet hole 1b of the sheet film comprising a resin, a metal foil, or a laminate of a resin and a metal foil, of the liquid-accommodating tool 2 installed between the capsule main body 1 and the cap 4 provided with the nozzle 4a; and in the capsule for dental restoration material of the example shown in FIG. 8, the sheet film comprising a resin, a metal foil, or a laminate of a resin and a metal foil, of the liquid-accommodating tool 2 installed with the clip in the outside of the aperture hole provided on the side surface of the capsule main body 1 is ruptured and broken with respect to a portion in the aperture hole side of the liquid-accommodating tool 2 by pushing the clip toward the direction of the mixing compartment 1a.

Further, in order to mix the powder component A and the liquid component B within the mixing compartment 1a of the capsule for dental restoration material, an operation for holding the capsule for dental restoration material within the capsule holding chamber 7 of the mixer for capsule for dental restoration material according to the present invention is carried out. Any of the operation for making the liquid component B within the liquid-accommodating tool 2 flow into the mixing compartment 1a of the capsule main body 1 and the operation for holding the capsule for dental restoration material within the capsule holding chamber 7 of the mixer for capsule for dental restoration material according to the present invention may be carried out in advance. However, when there is no device for making the liquid component B within the liquid-accommodating tool 2 flow into the mixing compartment 1a of the capsule main body 1 in the capsule for dental restoration material held within the capsule holding chamber 7 of the mixer for capsule for dental restoration material, an operation for making the liquid component B within the liquid-accommodating tool 2 flow into the mixing compartment 1a of the capsule main body 1 is carried out in advance.

Next, an operation in which the lid or the like is closed to render the capsule holding chamber 7 in a sealed state, the air inside the capsule holding compartment 7 is sucked by the vacuum device 10 to render the capsule holding compartment 7 in vacuo, and the air within the mixing compartment 1a of the capsule for dental restoration material held within the capsule holding compartment 7 is discharged out through the air-permeable filter 1c is carried out. During this operation, in the case where the vacuum device 10 is provided with the vacuum control unit for controlling a decompression degree and/or a decompression time, a suitable condition for the decompression degree and/or the decompression time is selected and set up depending on the kind of the dental restoration material comprising the powder component A and the liquid component B to be mixed, or the quantity of the dental restoration material to be mixed.

After the decompression degree within the mixing compartment 1a of the capsule for dental restoration material held within the capsule holding compartment 7 has reached a desired condition, an operation in which the capsule holding compartment 7 itself is subjected to a circular motion in the state that the longitudinal direction of the capsule holding compartment 7 is kept in a constant direction by the rotating unit 8 of capsule holding compartment, thereby mixing the powder component A and the liquid component B within the mixing compartment 1a of the capsule for dental restoration material. During this operation, in the case of an embodiment in which the rotating unit 8 of capsule holding compartment is controlled by the driving control unit for making its rotation number and/or rotation time variable, a suitable condition for the rotation number and/or the rotation time is selected and set up depending on the kind of the dental restoration material comprising the powder component A and the liquid component B to be mixed, or the quantity of the dental restoration material to be mixed.

In the case of an embodiment in which the rotating unit 8 of capsule holding compartment is constituted of the rotating table 8b that is pivoted rotatably to the fixed axis 8a and is rotated by the driving unit 9, the axis 8c for capsule holding compartment that is pivoted rotatably to the rotating table 8b in a position far from the fixed axis 8a by a predetermined distance and has the capsule holding compartment 7 fixed thereto, and the rotation power transmitting unit 8d for connecting the fixed axis 8a to the axis 8c for capsule holding compartment such that when the axis 8c for capsule holding compartment goes a round centering the fixed axis 8a, the axis 8c for capsule holding compartment makes one revolution, when the rotating table 8b pivoted to the fixed axis 8a is rotated by the driving unit 9 via the pulley 8bb, the axis 8c for capsule holding compartment undergoes a circular motion so as to draw a regular circle centering the center of axis of the fixed axis 8a. At this time, when the axis 8c for capsule holding compartment goes a round centering the fixed axis 8a by means of the rotation power transmitting unit 8d constituted of the pulley 8cb provided on the axis 8c for capsule holding compartment or in the capsule holding compartment 7, the pulley 8aa fixed to the fixed axis 8a and having the same diameter as the pulley 8cd, and the timing belt for connecting the both pulleys 8aa and 8cb to each other, the axis 8c for capsule holding compartment makes one revolution. Accordingly, the capsule holding compartment 7 fixed to the axis 8c for capsule holding compartment undergoes a circular motion on the rotating table 8b so as to draw a regular circle centering the center of axis of the fixed axis 8a in a state that the longitudinal direction of the capsule holding compartment 7 is always kept in a constant direction.

Thus, the powder component A and the liquid component B within the mixing compartment 1a of the capsule for dental restoration material held within the capsule holding compartment 7 to be subjected to a circular motion in the state that its longitudinal direction is kept in a constant direction and rendered in vacuo by the vacuum device 10 are mixed with each other so as to go a round along the inner surface of the mixing compartment 1a of the capsule for dental restoration material while being pressed to and crawling on the inner surface of the mixing compartment 1a by a centrifugal force as shown in FIG. 4. Accordingly, the mixture becomes one in a good state where no air bubbles exist within a short period of time.

After mixing of the powder component A and the liquid component B have been completed, the vacuum of the capsule holding chamber 7 is released, and the capsule for dental restoration material is then taken out from the capsule holding compartment 7 and is installed separately in an exclusive applier (not shown). Thereafter, the plunger 3 is moved toward the side of the outlet hole 1b of the capsule main body 1 by means of a push rod of the applier. At this time, in the capsule for dental restoration material of the example shown in FIG. 7, a portion in the opposite side to the outlet hole 1b of the sheet film comprising a resin, a metal foil, or a laminate of a resin and a metal foil, of the liquid-accommodating tool 2 is broken through by means of the through rod 5 set within the nozzle 4a provided on the center axis of the cap 4, and the through rod 5 is then taken out from the nozzle 4a. Further, in the capsule for dental restoration material of the embodiment shown in FIG. 8, the nozzle 4a is rotated to a position shown by a broken line, thereby connecting the outlet hole 1b of the capsule main body 1 to the nozzle 4a.

Thus, when the plunger 3 is moved toward the side of the outlet hole 1b of the capsule main body 1 by pushing with the push rod of the applier, the mixture within the mixing compartment 1a of the capsule main body 1 is extruded toward the outlet hole 1b of the capsule main body 1 in the state that no air bubbles are present and administered to a restoration site of a tooth from the nozzle 4a. In this case, in the capsule for dental restoration material of the embodiment shown in FIG. 5, the rod-like protrusion 3a of the plunger 3 penetrates through the outlet hole 1b of the capsule main body 1 and breaks through the air-permeable filter 1c installed between the capsule main body 1 and the cap 4 provided with the nozzle 4a. Further, in the capsule for dental restoration material of the embodiment shown in FIG. 6, when the rod-like protrusion 3a of the plunger 3 penetrates through the outlet hole 1b of the capsule main body 1 and breaks through a portion in the opposite side to the outlet hole 1b of the sheet film comprising a resin, a metal foil, or a laminate of a resin and a metal foil, of the liquid-accommodating tool 2 installed between the capsule main body 1 and the cap 4 provided with the nozzle 4a, the mixture is administered to a restoration site of a tooth from the nozzle 4a.

As described above in detail, the mixer for capsule for dental restoration material according to the present invention does not have a configuration in which the powder component and the liquid compartment of the dental restoration material are mixed with each other within the mixing compartment of the capsule for dental restoration material by shaking through a reciprocating motion but has a configuration in which in the state of keeping the longitudinal direction of the capsule holding compartment for holding the capsule for dental restoration material in a constant direction such that the air can be discharged out from the air-permeable filter, the capsule holding compartment itself is subjected to a circular motion, thereby mixing the powder component and the liquid component within the mixing compartment of the capsule for dental restoration material. Accordingly, a noise generated during the mixing can be made small. Thus, the mixer for capsule for dental restoration material according to the present invention does not disturb the progress of the therapy by hindering the communication between an operator and an assistant during the therapy of a patient. Further, a dental restoration material in a good state where no air bubbles exist in the resulting mixture can be obtained within a short period of time and with a good efficiency.

Further, in the mixer for capsule for dental restoration material having such a configuration, when the rotating unit of capsule holding compartment is constituted of a rotating table that is pivoted rotatably to a fixed axis and is rotated by the driving unit, an axis for capsule holding compartment that is pivoted rotatably to the rotating table in a position far from the fixed axis by a predetermined distance and has the capsule holding compartment fixed thereto, and a rotation power transmitting unit for connecting the fixed axis to the axis for capsule holding compartment such that when the axis for capsule holding compartment goes a round centering the fixed axis, the axis for capsule holding compartment makes one revolution, the capsule holding compartment itself can be subjected to a smooth circular motion in the state that the longitudinal direction of the capsule holding compartment is kept in a constant direction.

Moreover, when the driving unit is controlled by a driving control unit for making its rotation number and/or rotation time variable, or when the vacuum device is provided with a vacuum control unit for controlling a decompression degree and/or a decompression time, since the rotation number and/or the rotation time, or the decompression degree and/or the decompression time, of the capsule holding compartment can be controlled to a suitable condition depending on the dental restoration material comprising various kinds of the powder component and the liquid component to be mixed, or on the quantity of the dental restoration material to be mixed, not only a failure by over-mixing or short-mixing during the mixing works can be prevented, but also a dental restoration material in a good state can be easily obtained only through a simple operation by an operator to set up a suitable condition.

Still further, when the vacuum device and the capsule holding compartment are connected to each other by a passage respectively provided in the fixed axis, the rotating table and the axis for capsule holding compartment, not only the air within the capsule holding compartment can be stably discharged out, but also the durability of the whole of the apparatus of the present invention increases. Also, when the vacuum device is an ejector connected to a compressed air supply device of dental unit, since the compressed air supply device of dental unit that is placed in a dental clinic can be used as a power source as it stands, the configuration of the apparatus of the present invention can be made inexpensive and simple.

In the light of the above, the mixer for capsule for dental restoration material according to the present invention, which possesses various advantages, is greatly valuable in contributing to the dental field.

While the invention has been described in detail and with reference to specific embodiments thereof, it will be apparent to one skilled in the art that various changes and modifications can be made therein without departing from the spirit and scope thereof.

What is claimed is:

1. A mixer for capsule for dental restoration material to be used for mixing a powder component and a liquid component of a dental restoration material within a mixing compartment of a capsule for dental restoration material having an air-permeable filter, which does not pass the powder component and the liquid component through but can ventilate out air within the mixing compartment, placed in a site connecting the inside of the mixing compartment to the outside, the mixer comprising:

a capsule holding compartment for holding the capsule for dental restoration material such that the air within the mixing compartment can be discharged out from the air-permeable filter;

a rotating unit of the capsule holding compartment for subjecting the capsule holding compartment itself to a circular motion in the state that the longitudinal direction of the capsule holding compartment is kept in a constant direction;

a driving unit for driving the rotating unit of capsule holding compartment; and a vacuum device connected to the capsule holding compartment.

2. The mixer for capsule for dental restoration material according to claim 1, wherein the rotating unit of the capsule holding compartment is constituted of a rotating table that is pivoted rotatably to a fixed axis and is rotated by the driving unit, an axis for the capsule holding compartment that is pivoted rotatably to the rotating table in a position far from the fixed axis by a predetermined distance and has the capsule holding compartment fixed thereto; and a rotation power transmitting unit for connecting the fixed axis to the axis for the capsule holding compartment such that when the axis for the capsule holding compartment rotates about the fixed axis, the axis for the capsule holding compartment makes one revolution.

3. The mixer for capsule for dental restoration material according to claim 1, wherein the vacuum device and the capsule holding compartment are connected to each other by a passage respectively provided in the fixed axis, the rotating table and the axis for capsule holding compartment.

4. The mixer for capsule for dental restoration material according to claim 1, wherein the driving unit is controlled by a driving control unit for making its rotation number and/or rotation time variable.

5. The mixer for capsule for dental restoration material according to claim 1, wherein the vacuum device is provided with a vacuum control unit for controlling a decompression degree and/or a decompression time.

6. The mixer for the capsule for dental restoration material according to claim 1, wherein the vacuum device includes an ejector connected to a compressed air supply device of a dental unit.

* * * * *